(12) United States Patent
Ingelbrecht et al.

(10) Patent No.: US 7,081,432 B2
(45) Date of Patent: Jul. 25, 2006

(54) ALKYLATION CATALYST AND METHOD FOR MAKING ALKYLATED PHENOLS

(75) Inventors: Hugo G. E. Ingelbrecht, Essen (BE); David Parillo, Schenectady, NY (US); Mukund Parthasarathy, Delmar, NY (US); Gert-Jan Schoenmakers, Prinsenbeek (NL); Geuch Zijlma, Goes (NL)

(73) Assignee: General Electric Company, Pittsfield, MA (US)

( * ) Notice: Subject to any disclaimer, the term of this patent is extended or adjusted under 35 U.S.C. 154(b) by 161 days.

(21) Appl. No.: 10/604,311

(22) Filed: Jul. 10, 2003

(65) Prior Publication Data

US 2005/0009697 A1    Jan. 13, 2005

(51) Int. Cl.
*B01J 21/10* (2006.01)
*B01J 23/745* (2006.01)

(52) U.S. Cl. ...................... 502/340; 568/804
(58) Field of Classification Search ............... 502/340; 568/804

See application file for complete search history.

(56) References Cited

U.S. PATENT DOCUMENTS

| 3,306,874 A | 2/1967 | Hay |
| 3,306,875 A | 2/1967 | Hay |
| 3,446,856 A | 5/1969 | Hamilton, Jr. ............ 260/620 |
| 3,707,569 A | 12/1972 | van Sorge |
| 3,764,630 A | 10/1973 | Van Sorge |
| 3,790,641 A | 2/1974 | Oshima et al. |
| 3,843,606 A | 10/1974 | Van Sorge |
| 3,873,628 A | 3/1975 | Van Sorge |
| 3,953,529 A | 4/1976 | Yonemitsu et al. |
| 3,962,126 A | 6/1976 | Pecak |
| 3,962,181 A | 6/1976 | Sakauchi et al. |
| 3,968,172 A | 7/1976 | Ichikawa et al. |
| 3,972,828 A | 8/1976 | Van Sorge |
| 3,972,836 A | 8/1976 | Van Sorge |
| 3,974,229 A | 8/1976 | Van Sorge ............ 260/621 R |
| 3,979,464 A | 9/1976 | Leach |
| 3,994,982 A | 11/1976 | Leach |
| 4,022,715 A | 5/1977 | Bornfriend |
| 4,022,843 A | 5/1977 | Leach |
| 4,024,195 A | 5/1977 | Yonemitsu et al. |
| 4,041,085 A | 8/1977 | Frabetti, Jr. ............ 260/621 R |
| 4,048,239 A | 9/1977 | Smith ................ 260/624 C |
| 4,083,828 A | 4/1978 | Olander |
| 4,085,150 A | 4/1978 | Smith |
| 4,092,294 A | 5/1978 | Bennett, Jr. et al. |
| 4,097,411 A | 6/1978 | van Sorge |
| 4,126,750 A | 11/1978 | Poe et al. |
| 4,128,728 A | 12/1978 | Arnold et al. |
| 4,140,773 A | 2/1979 | Stowell et al. |
| 4,165,439 A | 8/1979 | Smith |
| 4,179,411 A | 12/1979 | Broersma et al. |
| 4,201,880 A | 5/1980 | van Sorge |
| 4,208,537 A | 6/1980 | Kawamata et al. |
| 4,215,229 A | 7/1980 | Greco |
| 4,225,732 A | 9/1980 | Dabrowski |
| 4,227,023 A | 10/1980 | Kawamata et al. |
| 4,227,024 A | 10/1980 | Leach |
| 4,269,735 A | 5/1981 | Leach |
| 4,283,574 A | 8/1981 | Leach |
| 4,290,924 A | 9/1981 | Leach |
| 4,322,566 A | 3/1982 | Leach |
| 4,329,517 A | 5/1982 | Taniguchi et al. |
| 4,351,958 A | 9/1982 | Takahata et al. |
| 4,361,709 A | 11/1982 | Kawamata et al. |
| 4,375,566 A | 3/1983 | Kawamata et al. |
| 4,386,226 A | 5/1983 | Adey et al. |
| 4,418,224 A | 11/1983 | Bennett et al. |
| 4,452,915 A | 6/1984 | Dabrowski |
| 4,454,357 A | 6/1984 | Inoue et al. |
| 4,458,031 A | 7/1984 | Battista et al. |
| 4,460,702 A | 7/1984 | Smith |
| 4,469,908 A | 9/1984 | Burress |
| 4,471,149 A | 9/1984 | Adey et al. |
| 4,475,001 A | 10/1984 | Leston |
| 4,476,329 A | 10/1984 | Chambers et al. |
| 4,482,758 A | 11/1984 | Seig |
| 4,517,389 A | 5/1985 | Katsumata et al. |
| 4,528,407 A | 7/1985 | Smith |
| 4,533,650 A | 8/1985 | Courty et al. |
| 4,547,480 A | 10/1985 | Bennett, Jr. et al. ......... 502/159 |
| 4,554,266 A | 11/1985 | Bennett et al. ............. 502/344 |
| 4,554,267 A | 11/1985 | Chambers et al. .......... 502/340 |
| 4,560,810 A | 12/1985 | Talley et al. |
| 4,572,778 A | 2/1986 | Ward |
| 4,590,307 A | 5/1986 | Bennett, Jr. et al. |
| 4,605,766 A | 8/1986 | Hargis |
| 4,644,086 A | 2/1987 | Voges et al. |
| 4,677,089 A | 6/1987 | Bennett, Jr. et al. |
| 4,720,478 A | 1/1988 | Voges et al. |
| 4,753,913 A | 6/1988 | Lenz et al. |
| 4,814,083 A | 3/1989 | Ford et al. |
| 4,822,836 A | 4/1989 | Wroczynski |
| 4,851,591 A | 7/1989 | Battista et al. |
| 4,874,810 A | 10/1989 | Lee, Jr. et al. |
| 4,876,398 A | 10/1989 | Lin et al. |
| 4,900,708 A | 2/1990 | Bennett et al. ............. 502/340 |
| 4,912,264 A | 3/1990 | Takeshita et al. |

(Continued)

FOREIGN PATENT DOCUMENTS

EP    0 129 065    5/1984

(Continued)

Primary Examiner—Brian Davis

(57) ABSTRACT

An alkylation catalyst comprises a metal oxide wherein the catalyst has a surface area to volume ratio of about 950 $m^2/m^3$ to about 4000 $m^2/m^3$.

22 Claims, No Drawings

U.S. PATENT DOCUMENTS

| | | | |
|---|---|---|---|
| 4,933,509 A | 6/1990 | Warner | 568/804 |
| 4,954,475 A | 9/1990 | Bennett, Jr. et al. | |
| 4,969,989 A | 11/1990 | Simpson | |
| 5,017,655 A | 5/1991 | Kase et al. | |
| 5,017,656 A | 5/1991 | Bopp | |
| 5,059,727 A | 10/1991 | Ito | |
| 5,095,156 A * | 3/1992 | Radlowski et al. | 568/905 |
| 5,097,079 A | 3/1992 | Bennett, Jr. et al. | |
| 5,128,304 A | 7/1992 | Ito | |
| 5,175,375 A | 12/1992 | Chang et al. | |
| 5,227,342 A | 7/1993 | Anderson et al. | |
| 5,245,089 A | 9/1993 | Irick, Jr. et al. | |
| 5,321,105 A | 6/1994 | Rekers et al. | |
| 5,345,005 A | 9/1994 | Thakur et al. | |
| 5,371,306 A | 12/1994 | Woo et al. | |
| 5,434,326 A | 7/1995 | Gajda et al. | |
| 5,488,173 A | 1/1996 | Wang | |
| 5,563,106 A | 10/1996 | Binner et al. | |
| 5,622,684 A | 4/1997 | Pinnavaia et al. | |
| 5,672,558 A | 9/1997 | White et al. | |
| 5,795,559 A | 8/1998 | Pinnavaia et al. | |
| 5,840,271 A | 11/1998 | Carrazza et al. | |
| 5,847,237 A | 12/1998 | Yago et al. | |
| 5,856,592 A * | 1/1999 | Hagen | 568/902.2 |
| 5,874,374 A | 2/1999 | Ong | |
| 5,902,429 A | 5/1999 | Apte et al. | |
| 5,985,944 A | 11/1999 | Ishizaki et al. | |
| 5,986,138 A | 11/1999 | Satyavathi et al. | |
| 5,998,317 A | 12/1999 | Sterzel | |
| 6,024,899 A | 2/2000 | Peng et al. | |
| 6,037,295 A | 3/2000 | Satyavathi et al. | |
| 6,042,763 A | 3/2000 | Kumaoka | |
| 6,049,008 A | 4/2000 | Roberts et al. | |
| 6,054,627 A | 4/2000 | Thakur et al. | |
| 6,153,547 A | 11/2000 | Sterzel | |
| 6,187,981 B1 | 2/2001 | Marinangeli et al. | |
| 6,203,774 B1 | 3/2001 | Han et al. | |
| 6,218,335 B1 | 4/2001 | Okada et al. | |
| 6,261,987 B1 | 7/2001 | Watson et al. | |
| 6,291,724 B1 | 9/2001 | Braat | |
| 6,294,499 B1 | 9/2001 | Watson et al. | |
| 6,340,648 B1 | 1/2002 | Imura et al. | |
| 6,379,640 B1 | 4/2002 | VerNooy | |
| 6,395,674 B1 | 5/2002 | Fung et al. | |
| 6,395,871 B1 | 5/2002 | Watson et al. | 528/489 |
| 6,420,292 B1 | 7/2002 | Kumaoka | |
| 6,429,168 B1 | 8/2002 | VerNooy | |
| 6,436,861 B1 | 8/2002 | Suzuki et al. | |
| 6,448,458 B1 | 9/2002 | Marinangeli et al. | |
| 6,455,748 B1 | 9/2002 | Janssen et al. | |
| 6,492,300 B1 | 12/2002 | Watson et al. | |
| 6,503,863 B1 | 1/2003 | Fung et al. | |
| 6,512,029 B1 | 1/2003 | Gugumus | |
| 6,541,407 B1 | 4/2003 | Beall et al. | |
| 6,541,415 B1 | 4/2003 | Vaughn et al. | |
| 6,620,751 B1 | 9/2003 | Ogunwumi | |
| 6,620,908 B1 | 9/2003 | Watson et al. | |
| 6,642,164 B1 | 11/2003 | Akaishi | |
| 6,649,802 B1 | 11/2003 | Frame et al. | |
| 6,657,022 B1 | 12/2003 | Williams et al. | |
| 6,667,261 B1 | 12/2003 | Anshits et al. | |
| 6,667,274 B1 | 12/2003 | Hawley et al. | |
| 6,743,747 B1 | 6/2004 | Xu et al. | |
| 2002/0128432 A1 | 9/2002 | Watson et al. | 528/489 |
| 2003/0073572 A1* | 4/2003 | Parrillo et al. | 502/150 |
| 2003/0125586 A1 | 7/2003 | Sankarasubbier et al. | |

FOREIGN PATENT DOCUMENTS

| | | |
|---|---|---|
| EP | 438329 A1 | 7/1991 |
| EP | 0785180 A2 | 7/1997 |
| EP | 0 987 220 | 9/1998 |
| WO | WO 84/01146 | 3/1984 |
| WO | WO 0138223 A1 | 5/2001 |
| WO | WO01/64334 | 9/2001 |

* cited by examiner

US 7,081,432 B2

ALKYLATION CATALYST AND METHOD FOR MAKING ALKYLATED PHENOLS

BACKGROUND OF INVENTION

This disclosure relates to alkylation catalysts and in particular to alkylation catalysts containing magnesium oxide or iron oxide, their methods of preparation and use in alkylation reactions.

Ortho-alkylated hydroxy aromatic compounds are useful for a variety of purposes. For example, ortho-cresol is a useful disinfectant and wood preservative. It is often prepared by the vapor-phase reaction of a phenol with methanol. In another alkylation reaction, ortho-cresol and phenol can both be converted into 2,6-xylenol. This xylenol monomer can be polymerized to form poly(2,6-dimethyl-1,4-phenylene)ether, which is the primary component in certain high-performance thermoplastic products.

Alkylated hydroxy aromatic compounds are usually prepared by the alkylation of the precursor hydroxy aromatic compound with a primary or secondary alcohol. The alkylation must be carried out in the presence of a suitable catalyst, such as a magnesium-based or iron-based compound.

A great deal of attention has been paid to optimizing the performance of magnesium-based catalysts in an industrial setting. Usually, it is very important for the catalyst to have high activity, i.e., it must have as long of an active life as possible. Moreover, the catalyst must have very good ortho-selectivity. Many of the ortho-alkylation catalysts used in the past produced a high proportion of para-alkylated products of marginal utility.

As an illustration, the alkylation of phenol with methanol in the presence of a magnesium oxide catalyst yields ortho-cresol (o-cresol) and 2,6-xylenol, which are desirable products. However, the alkylation reaction may also produce substantial amounts of para-substituted compounds, such as para-cresol (p-cresol), 2,4-xylenol, and mesitol (2,4,6-trimethylphenol). In some end use applications, these para-substituted compounds are much less useful than the corresponding compounds containing unsubstituted para positions.

While improvements in selectivity, activity and catalyst life have been made, there is an ongoing need for improved selectivity, activity and catalyst life in order to improve the efficiency of the alkylation process.

SUMMARY OF INVENTION

An alkylation catalyst comprising a metal oxide wherein the catalyst has a surface area to volume ratio of about 950 $m^2/m^3$ to about 4000 $m^2/m^3$ and/or an aspect ratio of about 0.7 to about 1.0.

An alkylation method comprising reacting a hydroxy aromatic compound with an alkyl alcohol in the presence of an alkylation catalyst comprising a metal oxide wherein the alkylation catalyst has a surface area to volume ratio of about 950 $m^2/m^3$ to about 4000 $m^2/m^3$ and/or an aspect ratio of about 0.7 to about 1.0.

DETAILED DESCRIPTION

Alkylated hydroxy aromatic compounds are manufactured by vapor phase reaction of an alkyl alcohol and hydroxy aromatic compound in the presence of an alkylation catalyst. It has been unexpectedly discovered that employing a catalyst having a surface area to volume ratio of about 950 to about 4000 $m^2/m^3$ and/or an aspect ratio of about 0.7 to about 1.0 improves the selectivity of the reaction. The surface area to volume ratio and/or aspect ratio increases the unpacked bulk density of the catalyst. The increase in unpacked bulk density results in an increase in the amount of catalyst that can be loaded into the reactor which surprisingly does not have a negative impact on selectivity and productivity and increases the time between catalyst changeouts thus increasing overall efficiency.

Pellet is defined herein as a small, densely packed mass of catalyst with no restriction with regard to geometry. Unpacked bulk density is defined herein as the density of randomly arranged pellets in a given volume. This is in contrast to a packed bulk density, which can be defined as the density of non-randomly arranged pellets in a given volume. Both of these are in contrast to pellet density, which is the average density of each pellet (weight per unit volume).

Hydroxy aromatic compounds include aromatic compounds having at least one hydroxy functional group and 6 to about 20 carbons. The hydroxy aromatic compound may comprise one aromatic ring or multiple aromatic rings that may be fused or unfused. The hydroxy aromatic compound has one or more ortho hydrogens. Additionally, the hydroxy aromatic compound may be substituted at the meta- and/or para- positions relative to the hydroxy functional group. Preferred hydroxy aromatic compounds include phenol and o-cresol.

Alkyl alcohols include saturated and unsaturated alkyl alcohols having one to about ten carbons. The alkyl alcohol may be branched or unbranched, primary or secondary. Specific examples of the alkyl alcohol include methyl alcohol, ethyl alcohol, isopropyl alcohol, n-propyl alcohol, n-butyl alcohol, isobutyl alcohol, tert-butyl alcohol, and the like, as well as combinations comprising at least one of the above mentioned alkyl alcohols. A preferred alkyl alcohol is methyl alcohol (methanol).

The alkylation catalyst comprises, as a main constituent, at least one metal oxide. The metal oxide can be obtained from a metal oxide precursor comprising a magnesium reagent, an iron reagent or a mixture of the foregoing. Any magnesium reagent which yields magnesium oxide can be used. Likewise, any iron reagent which yields iron oxide can be used. Preferred magnesium reagents include, but are not limited to, magnesium oxide, magnesium hydroxide, magnesium carbonate, magnesium nitrate, magnesium sulfate, magnesium carbonate, basic magnesium carbonate, magnesium acetate, and mixtures of the foregoing. The magnesium reagent is typically in the form of a powder. Basic magnesium carbonate is a preferred magnesium reagent. Basic magnesium carbonate is sometimes referred to as "magnesium carbonate hydroxide". Those skilled in the art understand that the exact formula for basic magnesium carbonate varies to some extent.

Examples of iron reagents used for the preparation of the catalyst include, but are not limited to, ferric nitrate, ferric sulfate, ferric chloride, ferrous nitrate, ferrous sulfate and ferrous chloride. Of these, ferric nitrate is particularly preferred. Furthermore, the iron oxides can be in any form of FeO, $Fe_2O_3$, $Fe_3O_4$, or mixtures of the foregoing.

In one embodiment, the level of chlorides in the magnesium reagent is less than about 250 parts per million (ppm), preferably less than about 125 ppm, and more preferably less than about 100 ppm. (As used herein, "chlorides" refers to chloride ions, which are often present in the form of a salt). The level of calcium in the magnesium reagent should be less than about 2500 ppm, and preferably, less than about 1000 ppm. In some embodiments, the level of calcium is less than about 750 ppm. (These levels of impurities can alternatively be specified with respect to the magnesium oxide-form which results from calcination. The impurity threshold levels in the calcined oxide would be approximately twice those for a basic magnesium carbonate reagent, e.g., less than about 500 ppm chlorides and less than about 5000 ppm calcium, in the broadest embodiment).

The levels of chlorides and calcium in the magnesium reagent can be determined by common analytical methods. For example, calcium levels can be determined by a titration technique or by some form of spectroscopy, e.g., inductively coupled plasma atomic emissions spectroscopy. Chloride levels are usually determined by titration or by ion chromatography. Magnesium reagents of this type can be made available by commercial sources upon request.

The alkylation catalyst is formed by dry-blending the metal oxide precursor with at least one filler and an optional pore former. The term "filler" is meant to encompass various lubricants, binders and fillers that are known in the art for incorporation into this type of catalyst. The total amount of filler present in the catalyst composition is usually up to about 20% by weight, based on the total weight of filler and magnesium reagent. In some embodiments, the level of filler is up to about 10% by weight. Examples of fillers used in the catalyst composition include graphite and polyphenylene ether (PPE). The polyphenylene ether is usually used in an amount of up to about 10% by weight, based on total weight, while the graphite is usually employed in an amount of up to about 5% by weight.

The optional pore former is a substance capable of aiding the formation of pores in the catalyst and is preferably selected from the group consisting of waxes and polysaccharides. The waxes can be selected from one or more of paraffin wax, polyethylene wax, microcrystalline wax, montan wax, and the like. The polysaccharide may be selected from one or more of cellulose, carboxyl methyl cellulose, cellulose acetate, starch, walnut powder, citric acid, polyethylene glycol, oxalic acid, stearic acid and the like. Also useful are anionic and cationic surfactants, typically long chain ($C_{10-28}$) hydrocarbons containing neutralized acid species, e.g., carboxylic acid, phosphoric acid, and sulfonic acid species.

The amount of the pore former is that amount which provides for a distribution of pore diameters of about 100 to about 400 Angstroms after calcination and typically ranges between about 100 ppm to 10 wt %, usually between about 100 ppm and 5 wt %, and preferably in amounts up to about 2 wt %, based on the total weight of metal oxide precursor, filler and pore former. In some embodiments the alkylation catalyst will have a bimodal distribution of pores. It is believed that the first and smaller diameter pore distribution is obtained from the metal oxide precursor during the calcination process, i.e. these pores are of similar dimension to those obtained from calcination of the metal oxide precursor not containing the pore former. The second and larger diameter pore distribution is believed to be the result of the addition and calcination of the pore former reagent itself, i.e. these pore diameters would not be found in substantial quantities after calcination of a metal oxide precursor not containing the pore former. Preferably, the bimodal distribution of pores has a first distribution of pores wherein the first distribution has an average pore diameter less than 100 angstroms and a second distribution of pores wherein the second distribution has an average diameter greater than 100 angstroms and less than 400 Angstroms.

As used in this disclosure, the term "dry blending" refers to the general technique in which the individual ingredients are initially mixed together in the dry state, without resorting to any "wet" techniques, such as suspension blending or precipitation. Any type of mechanical mixer or blender can be used, such as a ribbon blender. Those skilled in the art are familiar with the general parameters for dry-blending this type of material. The ingredients should be mixed until an intimate blend is obtained, with the filler and optional pore former being well-dispersed. The blending time is typically in the range of about 10 minutes to about 2 hours, at a shaft speed of about 5 rotations per minute (rpm) to about 60 rpm.

After dry-blending of the metal oxide precursor, filler (or multiple fillers) and optional pore former is complete, the blended, solid catalyst composition is in the form of a powder. The powder usually has a bulk density in the range of about 0.1 grams per cubic centimeter ($g/cm^3$) to about 0.5 $g/cm^3$, and preferably in the range of about 0.25 $g/cm^3$ to about 0.5 $g/cm^3$. The powder then typically undergoes further processing, prior to being shaped into a desired form. Non-limiting examples of the additional processing steps include sieving (to obtain a more narrow particle distribution), milling, and compressing.

In some preferred embodiments, the catalyst composition is compacted after dry-blending. Compacting equipment is known in the art. Commercial compacting systems are available from various sources, such as Allis-Chalmers; Gerteis Macshinen, Jona, Switzerland; and Fitzpatrick Co., Elmhurst, Ill. The compactors usually function by feeding the powdered material through rollers.

One specific example of a suitable compactor unit is known as the "Chilsonator"™. In such a system, the catalyst powder is first fed to compaction rolls by a rapidly-turning vertical feed screw. The feed screw forces the powder into a roll nip. The rolls compress the material into a continuous solid sheet.

In most embodiments, the catalyst composition is deaerated after dry-blending, and prior to additional processing. This step is especially important in those instances in which the composition must subsequently pass through compaction rollers. Deaeration further increases the bulk density of the material by forcibly removing entrained gas (primarily air) from within the powder. Deaeration systems are known in the art and available from various sources. Vacuum deaeration is one common technique. The vacuum can be applied at various points along the passage of the powder from the blending unit to other processing operations. Usually, the vacuum is applied at a point very close to (and preceding) the location of compaction rollers. The strength of the vacuum will depend on various factors, such as the amount of powder being processed; its compressibility; the type of fillers contained therein, and the density of the powder. Usually, the vacuum strength is in the range of about 5 inches (12.7 cm) mercury to about 25 inches (63.5 cm) mercury.

The solid sheets of catalyst material formed by compaction may then be granulated by various techniques. The granulated material is typically size-separated. The desired catalyst granules can then be conveyed immediately to a shaping operation, or to a storage facility. The shape of the catalyst is not critical for this invention and will depend on the manner in which the catalyst is being used for subsequent alkylation operations. Very often, the catalyst is compressed into a pellet or "tablet". Conventional pelletizing equipment can accomplish this task (e.g., a Betapress), as described in U.S. Pat. No. 4,900,708. The shaped catalyst composition is then calcined. Calcination is usually carried out by heating the catalyst at a temperature sufficient to convert the metal oxide precursor to metal oxide, which is the active species in the catalyst. Calcination increases the surface area of the catalyst. The calcination temperature may vary somewhat, but is usually in the range of about 350° C. to about 550° C. The calcination atmosphere may be oxidizing, inert, or reducing. Alternatively, the catalyst can be calcined at the beginning of the alkylation reaction. In other words, calcination can take place in the presence of the alkylation feed materials, i.e., the hydroxy aromatic compound and the alkyl alcohol.

The surface area of the catalyst pellets is about 100 square meters per gram ($m^2/g$) to about 300 $m^2/g$, based on BET analysis. The uncalcined pellets have pellet density of about 1.3 $g/cm^3$ to about 2.1 $g/cm^3$. Within this range the pellets have a pellet density of greater than or equal to about 1.4 $g/cm^3$, preferably greater than or equal to about 1.6 $g/cm^3$. Also within this range the pellets have a pellet density of less than or equal to about 2.0 $g/cm^3$, preferably less than or equal to about 1.9 $g/cm^3$. It is known that with pellets having a surface area to volume ratio of less than about 950 $m^2/m^3$ the selectivity of the reaction decreases when pellet density increases above about 1.6 $g/cm^3$. Surprisingly, pellets having a surface area to volume ratio of greater than about 950 $m^2/m^3$ can have pellet densities greater than or equal to about 1.6 $g/cm^3$ without a negative impact on reaction selectivity.

In one embodiment, the catalyst pellets have a surface area to volume ratio of about 950 $m^2/m^3$ to about 4000 $m^2/m^3$. Within this range, the catalyst pellets preferably have a surface area to volume ratio greater than or equal to about 1100 $m^2/m^3$ and more preferably greater than or equal to about 1300 $m^2/m^3$. Also within this range the catalyst pellets have a surface area to volume ratio less than or equal to about 3800 $m^2/m^3$ and more preferably less than or equal to about 3000 $m^2/m^3$.

In another embodiment, the catalyst pellets have an aspect ratio of about 0.7 to about 1.0. Within this range, the aspect ratio is preferably greater than or equal to about 0.72 and more preferably greater than or equal to about 0.75. Also within this range, the aspect ratio is preferably less than or equal to about 0.95 and more preferably less than or equal to about 0.90. Aspect ratio is herein defined as the ratio of length to diameter or length to width.

The catalyst pellets have an unpacked bulk density of about 900 to about 1200 kilograms per cubic meter ($kg/m^3$). Within this range, the unpacked bulk density is preferably greater than or equal to about 920, more preferably greater than or equal to about 950 $kg/m^3$. Also within this range, the unpacked bulk density is preferably less than or equal to about 1180, more preferably less than or equal to about 1150 $kg/m^3$.

In one embodiment, the catalyst pellets have a diameter of about 1.0 to about 4.0 millimeters, and a height of about 2.0 to about 3.0 millimeters.

The alkyated hydroxy aromatic compound is formed by reacting a hydroxy aromatic compound with an alkyl alcohol in the presence of an alkylation catalyst comprising a metal oxide wherein the alkylation catalyst has a surface area to volume ratio of about 950 $m^2/m^3$ to about 4000 $m^2/m^3$, an aspect ratio of about 0.7 to about 1.0 or a combination of the foregoing. The temperature of the re-action is at least about 420° C., and preferably is about 440° C. to about 500° C. The alkylation reaction may be carried out in the presence of water vapor. The quantity of water vapor may be about 1 to about 35 weight percent (wt %), based on the total weight of the reactants, but is preferably about 5 to 25 wt %, based upon the total weight of the reactants.

In order to obtain a yield of ortho-alkylated products, at least one mole of the alcohol and preferably from 1 to 3 moles of the alcohol are used for each ortho-position on the phenol to be alkylated. For example, if phenol which has 2-ortho-hydrogens per molecule is to be methylated to produce a yield of 2,6-xylenol, it is desirable to use two to six moles of methanol for each mole of phenol, with higher yields and selectivities being obtained with the higher ratio of methanol to phenol.

The alkylation reaction is generally carried out in a reactor system well described in the state of the art. The vapors issuing from the reactor are condensed and the product is separated by conventional methods such as crystallization, distillation, etc. The reaction proceeds at atmospheric pressure, but pressures above or below may also be used.

The alkylation techniques are generally known in the art, and described in the above-referenced U.S. Pat. Nos. 4,554, 267 and 3,446,856. Suitable processes are also described in U.S. Pat. Nos. 4,933,509; 4,900,708; 4,554,266; 4,547,480; 4,048,239; 4,041,085; and 3,974,229.

Specific examples of alkylated aromatic hydroxy compounds include, but are not limited to, o-, m- and p-cresols; 2,3-, 2,4-, 2,5-, 3,4- and 3,5-xylenols; trimethylphenols; tetramethylphenols; n- and iso-propylphenols; n-, iso- and tert-butylphenols; and the like, as well as combinations and reaction products comprising at least one of the above mentioned alkylated aromatic hydroxy compounds. In addition, alkylated aromatic hydroxy compounds include aromatic compounds having at least two different alkyl substituent groups on the same aromatic ring are also usable.

Having described the invention in detail, the following examples are provided. The examples should not be considered as limiting the scope of the invention, but merely as illustrative and representative of making alkylated phenols.

EXAMPLES

Alkylation catalysts comprising magnesium oxide were formed into pellets having two different sizes and calcined at 404° C. for 16 hrs under nitrogen flow at a WHSV of 0.12 g/g/hr. The pellet size of the calcined pellets used in the first example was 2.96 millimeters in diameter and 2.32 millimeters in height and the pellet size of the calcined pellet used in the second example was 4.45 millimeters in diameter and 2.95 millimeters in height. The pellets in the first example had an aspect ratio of 0.78 and a surface area to volume ratio of 1400 $m^2/m^3$. The pellets in the second example had an aspect ratio of 0.66 and a surface area to volume ratio of 900 $m^2/m^3$. The catalysts were loaded into a lab scale reactor for use in an alkylation reaction. The alklyation reaction employed a feed comprising methanol and phenol in a weight ratio of 1.4. The feed also contained 20% water by weight. The reaction temperature was about 440° C. and the pressure was 170 kPa. The WHSV during reaction was 2.1 g/g/hr.

Table 1 below summarizes the reaction selectivity, phenol usage and methanol usage obtained after more than 150 hours runtime. Selectivity is defined as (Effluent moles (p-cresol+2,4-xylenol+mesitol))/(Effluent moles (phenol+o-cresol+2,6-xylenol))×100. Phenol usage is defined as (phenol used/2,6 xylenol produced)×100. Methanol usage is defined as (methanol used/2,6 xylenol produced)×100.

TABLE 1

| Reaction time in hours | Selectivity | | Phenol Usage | | Methanol Usage | |
|---|---|---|---|---|---|---|
| | Ex. 1 | Ex. 2* | Ex. 1 | Ex. 2* | Ex. 1 | Ex. 2* |
| 167 | 0.026 | 0.029 | 78.92 | 79.23 | 60.88 | 61.67 |
| 173 | 0.025 | 0.029 | 78.85 | 79.21 | 60.96 | 61.72 |
| 191 | 0.023 | 0.027 | 78.77 | 79.14 | 60.79 | 61.75 |

*Comparative Example

Results in the above tables clearly shows the increased selectivity of the pellets having a 1400 m²/m³ surface area to volume ratio and a 0.78 aspect ratio over pellets having a 900 m²/m³ surface area to volume ratio and a 0.66 aspect ratio, and the strongly reduced phenol and methanol usage for the production of 2,6 xylenol.

Table 42 shows the unpacked bulk density (UPBD) determined for the pellets described above.

| UPBD in 45 millimeter tube (kg/m³) | |
|---|---|
| Example 1 | Example 2* |
| 1,063 | 802 |

*Comparative example

Results in above table clearly show the increased unpacked bulk density of the pellets having a 1400 m²/m³ surface area to volume ratio and a 0.78 aspect ratio over pellets having a 900 m²/m³ surface area to volume ratio and a 0.66 aspect ratio. The increases in the unpacked bulk density increase the amount of catalyst that can be loaded in the reactor compared to earlier catalysts. The increase in loading results in decreased catalyst material usage and a longer reactor cycle time, making the method more efficient.

All patents cited herein are incorporated by reference.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the invention scope thereof. It is, therefore intended that the invention not be limited to the particular embodiment disclosed as the best mode contemplated for carrying out this invention, but that the invention will include all embodiments falling within the scope of appended claims.

The invention claimed is:

1. An alkylation catalyst comprising a metal oxide wherein the catalyst has a surface area to volume ratio of about 950 m²/m³ to about 4,000 m²/m³ and further wherein the catalyst has a bimodal distribution of pores.

2. The catalyst of claim 1, wherein the metal oxide comprises magnesium oxide, iron oxide or a combination of the foregoing.

3. The catalyst of claim 1, wherein the catalyst further comprises filler.

4. The catalyst of claim 1, wherein the catalyst has pores with diameters of about 100 to about 400 Angstroms after calcination.

5. The catalyst of claim 1, wherein the catalyst is in the form of pellets having a surface area of about 100 square meters per gram to about 300 square meters per gram.

6. The catalyst of claim 1, wherein the uncalcined catalyst is in the form of pellets having a pellet density of about 1.30 to about 2.10 grams per cubic centimeter.

7. The catalyst of claim 1 having a surface areas to volume ratio of about 1100 to about 3800 m²/m³.

8. The catalyst of claim 1, wherein the catalyst has an unpacked bulk density of about 900 to about 1200 kilograms per cubic meter.

9. The catalyst of claim 1, wherein the catalyst is in the form of pellets having a diameter of about 1.0 to about 4.0 millimeters and a height of about 2.0 to about 3.0 millimeters.

10. An alkylation catalyst comprising a metal oxide wherein the catalyst has an aspect ratio of about 0.7 to about 1.0; and further wherein the catalyst has a bimodal distribution of pores; and further wherein the catalyst is in the form of pellets having a pellet density of about 1.3 to about 2.10 grams per cubic centimeter.

11. The catalyst of claim 10, wherein the metal oxide comprises magnesium oxide, iron oxide or a combination of the foregoing.

12. The catalyst of claim 10, wherein the catalyst further comprises a filler.

13. The catalyst of claim 10, wherein the catalyst has pares with diameters of about 100 to about 400 Angstroms after calcinations.

14. The catalyst of claim 10, wherein the catalyst is in the form of pellets having a surface area of about 100 square meters per gram to about 300 square meters per gram.

15. The catalyst of claim 10, having a surface area to volume ratio of about 950 to about 4000 m²/m³.

16. The catalyst of claim 10, wherein the catalyst has an unpacked bulk density of about 900 to about 1200 kilograms per cubic meter.

17. The catalyst of claim 10, wherein the catalyst is in the form of pellets having a diameter of about 1.0 to about 4.0 millimeters and a height of about 2.0 to about 3.0 millimeters.

18. An alkylation catalyst comprising a metal oxide wherein the catalyst is in the form of pellets having a diameter of about 1.0 to about 4.0 millimeters and a height of about 2.0 to about 3.0 millimeters and further wherein the catalyst has a bimodal distribution of pores.

19. The catalyst of claim 18, wherein the metal oxide comprises magnesium oxide, iron oxide or a combination of the foregoing.

20. The catalyst of claim 18, wherein the catalyst further comprises filler.

21. The catalyst of claim 18, wherein the catalyst has pores with diameters of about 100 to about 400 Angstroms after calcination.

22. The catalyst of claim 18, wherein the catalyst has an unpacked bulk density of about 900 to about 1200 kilograms per cubic meter.

* * * * *

UNITED STATES PATENT AND TRADEMARK OFFICE
CERTIFICATE OF CORRECTION

PATENT NO. : 7,081,432 B2
APPLICATION NO. : 10/604311
DATED : July 25, 2006
INVENTOR(S) : Ingelbrecht et al.

It is certified that error appears in the above-identified patent and that said Letters Patent is hereby corrected as shown below:

Title Page:
(75) Inventors, delete "Parillo" and insert therefor -- Parrillo --

Column 8:
Line 32, before "with" delete "pares" and insert therefor -- pores --

Signed and Sealed this

Sixth Day of March, 2007

JON W. DUDAS
*Director of the United States Patent and Trademark Office*